United States Patent
Sianawati et al.

(10) Patent No.: US 8,691,726 B2
(45) Date of Patent: Apr. 8, 2014

(54) SYNERGISTIC COMBINATION OF A GLYPHOSATE COMPOUND AND ZPT

(75) Inventors: Emerentiana Sianawati, Vernon Hills, IL (US); Sudhakar Balijepalli, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 158 days.

(21) Appl. No.: 13/315,386

(22) Filed: Dec. 9, 2011

(65) Prior Publication Data

US 2012/0165194 A1 Jun. 28, 2012

Related U.S. Application Data

(60) Provisional application No. 61/425,999, filed on Dec. 22, 2010.

(51) Int. Cl.

| | | |
|---|---|---|
| *A01N 55/02* | (2006.01) | |
| *A01N 57/18* | (2006.01) | |
| *C09D 5/16* | (2006.01) | |
| *A01N 25/00* | (2006.01) | |
| *A01N 59/16* | (2006.01) | |
| *B05D 3/00* | (2006.01) | |
| *A01N 57/10* | (2006.01) | |
| *A01N 57/00* | (2006.01) | |

(52) U.S. Cl.
USPC .............. 504/126; 106/18.31; 106/18.27; 424/405; 424/641; 424/642; 427/384; 504/152; 504/206; 514/109; 514/114; 514/184; 514/188; 514/494

(58) Field of Classification Search
USPC .......... 504/126, 206, 152; 427/384, 406; 106/18.31, 18.27; 424/405, 641, 642; 514/109, 274, 184, 188, 114, 494
See application file for complete search history.

(56) References Cited

U.S. PATENT DOCUMENTS

| | | | |
|---|---|---|---|
| 5,158,596 | A | 10/1992 | Sherba et al. |
| 5,591,760 | A | 1/1997 | Hsu |
| 2004/0198714 | A1 | 10/2004 | Heer |
| 2004/0253194 | A1 | 12/2004 | Rioux et al. |

FOREIGN PATENT DOCUMENTS

| | | |
|---|---|---|
| WO | 9821962 | 5/1998 |
| WO | 9836904 | 8/1998 |
| WO | 2004057964 | 7/2004 |
| WO | 2008147404 | 12/2008 |

OTHER PUBLICATIONS

Ahmed A. Issa, "Interference of glyphosate with the shikimate pathway by cyanobacteria in chemostate culture", Microbios, vol. 100, No. 395, pp. 47-55 (1999).

*Primary Examiner* — John Pak
*Assistant Examiner* — Andriae M Holt
(74) *Attorney, Agent, or Firm* — Tifani M. Edwards

(57) ABSTRACT

A synergistic antimicrobial composition containing a glyphosate compound and zinc pyrithione is provided. Also provided is a method of inhibiting the growth of or controlling the growth of microorganisms in a building material by adding such a synergistic antimicrobial composition. Also provided is a coating composition containing such a synergistic antimicrobial composition, and a dry film made from such a coating composition.

4 Claims, No Drawings

SYNERGISTIC COMBINATION OF A GLYPHOSATE COMPOUND AND ZPT

This invention relates to combinations of biocides, the combinations having unexpectedly greater activity than would be expected for the use of both of the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, e.g., those resistant to some antimicrobial compounds. Combinations of different antimicrobial compounds are sometimes used to provide overall control of microorganisms in a particular end use environment. For example, WO 1998/121962 discloses combinations of 3-iodo-2-propynyl-butylcarbamate and zinc pyrithione, but this reference does not suggest any of the combinations claimed herein. Moreover, there is a need for additional combinations of antimicrobial compounds with relatively low impact on health and/or the environment. The problem addressed by this invention is to provide such additional combinations of antimicrobial compounds.

Antimicrobial compounds are sometimes included in liquid coating compositions that are applied to a substrate and that become dry films. It is desirable that such dry films control surface fungi and algae and that such dry films also present as little adverse effect as possible on health and the environment.

The following is a statement of the invention.

The first aspect of the present invention is a synergistic antimicrobial composition containing a glyphosate compound and zinc pyrithione is provided. A second aspect of the present invention is a method of inhibiting the growth of or controlling the growth of microorganisms in a building material by adding the synergistic antimicrobial composition of the first aspect of the present invention. A third aspect of the present invention is a coating composition containing a synergistic antimicrobial composition of the first aspect of the present invention.

A fourth aspect of the present invention is dry film made from a coating composition of the third aspect of the present invention.

The following is a detailed description of the invention.

As used herein, the following terms have the designated definitions, unless the context clearly indicates otherwise.

The term "antimicrobial compound" refers to a compound capable of inhibiting the growth of or controlling the growth of microorganisms; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The following abbreviations are used throughout the specification: ppm=parts per million by weight (weight/weight), mL=milliliter, ATCC=American Type Culture Collection, and MIC=minimum inhibitory concentration. Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present.

As used herein, "ZPT" is zinc pyrithione. When a ratio is said herein to be "X:1 or higher," it is meant that the ratio is Y:1, where Y is X or greater, and when a ratio is said herein to be "X:1 or lower," it is meant that the ratio is Z:1, where Z is X or less.

Glyphosate is N-(phosphonomethyl)glycine (registry number 1071-83-6). Glyphosate is a known herbicide that is approved in many jurisdictions for use for weed control on food crop plants. One measure of glyphosate's relatively low impact on the environment is shown by its relatively low activity against various algae. Some results showing the activity of glyphosate against various algae are as follows:

| Test[1] | Algae | 72 hr | 96 hr | 7 day |
|---|---|---|---|---|
| $E_bC_{50}$ | green algae (*Selenastrum capricornutum*) | 485 mg/l | | 13.8 mg/l |
| $E_rC_{50}$ | green algae (*Selenastrum capricornutum*) | 460 mg/l | | |
| $EC_{50}$ | marine algae (*Skeletonema costatum*) | | 1.3 mg/l | 0.64 mg/l |
| $EC_{50}$ | diatom (*Navicula pelliculosa*) | | | 42 mg/l |
| $EC_{50}$ | blue-green algae (*Anabaena flos-aquae*) | | | 15 mg/l |

[1]Notes:
$EC_n/EC_{50}$ Effective Concentration $EC_n$ is the concentration of a substance that affects n % of a population in a given period of time. $EC_{50}$ is widely used since it is the most accurate point in the concentration effect curve.
$E_bC_{50}$ Median effective concentration for biomass (algae): The concentration of a substance which reduces by 50% the increase of biomass compared with a control sample, over a specified time period.
$E_rC_{50}$ Median effective concentration for growth rate (algae): The concentration of a substance which reduces by 50% the growth rate of algal cells, compared with a control sample, over a specified time period.

The above data show that glyphosate has relatively low impact on algae, which indicates that glyphosate has relatively low impact the environment. This characteristic is considered desirable for an antimicrobial material that may be included in a coating composition.

The present invention involves the use of a glyphosate compound. As used herein "a glyphosate compound" means glyphosate or a glyphosate salt. A glyphosate salt is a metal salt of glyphosate. Suitable metals include alkali metals, alkaline earth metals, and transition metals. Glyphosate salts are preferred over glyphosate. More preferred are transition metal salts of glyphosate; most preferred is zinc glyphosate.

Glyphosate has relatively high solubility in water. This relatively high solubility in water is not preferred for an antimicrobial material that may be included in a coating composition or other building material, because dried coatings and building materials are exposed to water, which could tend to remove a highly soluble compound from the dried coating or the building material. Preferred are glyphosate salts that have solubility in water, at 20° C., of 3 g/l or less; more preferred is 1 g/l or less; more preferred is 0.3 g/l or less.

It is considered that glyphosate salts will have relatively low impact on health and the environment, because it is considered that glyphosate salts will have impact on health and the environment that is similar to the impact of glyphosate.

The present invention involves a composition that contains both a glyphosate compound and ZPT. It has been surprisingly found that such a composition is synergistically effective as a biocide. It has been especially surprisingly found that compositions that contain both zinc glyphosate and ZPT are synergistically effective as biocides.

The preferred weight ratio of ZPT to glyphosate compound is 0.1:1 to 10:1. In one preferred embodiment, the weight ratio of ZPT to glyphosate compound is 0.1:1 to 1:1. In another preferred embodiment, the weight ratio of ZPT to glyphosate compound is 1:1 to 10:1.

The mixture of glyphosate compound and ZPT may be included in a coating composition. Glyphosate compound and ZPT may be added to the coating composition separately or as a mixture or any combination thereof. Preferred coating compositions are liquid. Coating compositions may be aqueous or non-aqueous. Aqueous coating compositions contain 40% or more water by weight, based on the weight of the coating composition.

Among embodiments in which glyphosate compound and ZPT are included in a paint or other coating composition, preferred coating compositions are liquid compositions, especially compositions that contain dispersions of polymers in aqueous media.

In addition to paints and other coating compositions, the biocide combinations of the present invention are particularly useful in preservation of building materials, e.g., adhesives, caulk, joint compound, sealant, wallboard, etc., polymers, plastics, synthetic and natural rubber, paper products, fiberglass sheets, insulation, exterior insulating finishing systems, roofing and flooring felts, building plasters, bricks, mortar, gypsum board, wood products and wood-plastic composites. When a biocide combination of the present invention is present in a building material, it is preferred that some or all of the biocide combination be present at the surface of the building material or near enough to the surface of the building material to inhibit microbial growth on that surface.

In some embodiments, latex paints or other liquid coating compositions are used that contain the biocide combinations disclosed herein.

Coating compositions are designed so that a layer of the coating composition can readily be applied to a substrate and then dried or allowed to dry to form a dry film. Coating compositions contain a binder. Binders contain one or more of the following: one or more polymer, one or more oligomer, and/or one or more monomer. Oligomers and monomers in binders are designed to polymerize and/or crosslink during or after the formation of the dry film. Polymers in a binder may or may not be designed to crosslink during or after the formation of the dry film.

Coating compositions optionally contain one or more pigment. A pigment is a mineral or an organic substance in the form of small solid particles. Pigments provide full or partial opacity to the dry film.

The biocide combinations are useful for preservation of the dry film coating resulting after application of a paint or other liquid coating composition. Preferably, the antimicrobial composition is an aqueous latex paint comprising one or more of the biocide combinations disclosed herein, or the dry film coating resulting from application of the paint to a surface. An aqueous latex paint is an aqueous liquid coating composition in which the binder is an polymer in the form of a latex (i.e., in the form of polymer particles dispersed throughout the water). More preferred are aqueous latex paints in which the binder contains one or more acrylic polymer.

Typically, the amount of the biocide combinations of the present invention to control the growth of microorganisms is from 100 ppm to 10,000 ppm active ingredient. Preferably, the active ingredients of the composition are present in an amount of at least 300 ppm, preferably at least 500 ppm, preferably at least 600 ppm, preferably at least 700 ppm. Preferably, the active ingredients of the composition are present in an amount of no more than 8,000 ppm, preferably no more than 6,000 ppm, preferably no more than 5,000 ppm, preferably no more than 4,000 ppm, preferably no more than 3,000 ppm, preferably no more than 2500 ppm, preferably no more than 2,000 ppm, preferably no more than 1,800 ppm, preferably no more than 1,600 ppm. Concentrations mentioned above are in a liquid composition containing the biocide combinations; biocide levels in the dry film coating will be higher.

The present invention also encompasses a method for preventing microbial growth in building materials, especially in dry film coatings, by incorporating any of the claimed biocide combinations into the materials.

Typically, the antimicrobial compositions are used to inhibit growth of algae and/or fungi.

The composition of the present invention contains a glyphosate compound and ZPT. It is contemplated that some embodiments may contain one or more additional antimicrobial compound.

It is contemplated that zinc glyphosate shows unexpectedly synergistic antimicrobial action in comparison with results that would be expected from a combination of zinc and glyphosic acid.

The following are examples of the present invention.

Zinc Glyphosate was synthesized as follows.

First, pre-preparation was performed as follows. 15-20 g Glyphosate acid was dried in oven at 80-90° C. overnight. A 1 M solution of NaOH in deionized (DI) water was prepared.

Glyphosate solution was made as follows. 200 mL DI water was measured into 600 mL beaker containing stir bar. 15 g Glyphosate acid was slowly added to beaker of water while stirring on stir plate at medium speed. Temperature was raised up to 60-70° C. to dissolve the glyphosate; temperature was monitored with thermometer. 1M NaOH was added to bring pH up to 6.0. The glyphosate dissolved at a pH around 2.4. The mixture was agitated for 5-10 minutes.

A zinc solution was made as follows. 100 mL DI water was measured into 400 mL beaker containing stir bar. 36.25 g Zinc Chloride (Reagent Grade, >98%, Sigma-Aldrich, material #208086) was measured into weigh boat Zinc chloride was slowly added to water in beaker while mixing on stir plate. Solution was heated up to 65° C.

Zinc glyphosate solution was made as follows. Using a 9-inch Pasteur pipette, the zinc solution was added to the glyphosate solution. After each addition of a small amount of zinc solution to glyphosate solution, the precipitate dissolved before further zinc solution was added. When the precipitate would no longer dissolve, pH was adjusted up to 5. Remainder of zinc solution was poured into the glyphosate solution, and the mixture was stirred overnight.

NOTE: controlling the pH of the solution is extremely important for obtaining the desired product. During the preparations reported herein, care was taken not exceed pH value of 5.

Zinc Glyphosate Filtration was performed as follows.

Filtration apparatus was set up using a Buchner funnel and a filter flask connected with a flask seal and hooked up to a water-vacuum pump. A #41 Whatman™ filter paper was placed in the funnel. The pump was turned on, and DI water was poured onto filter paper to create vacuum. The Glyphosate, zinc slurry was slowly poured onto the filter paper and then washed once with hot (approximately 50° C.) DI water, and then rinsed twice with isopropyl alcohol (IPA).

The Zinc Glyphosate Final Preparation was performed as follows.

Filter paper containing zinc glyphosate precipitate was removed and placed in a large Pyrex™ dish. The dish was covered with metal foil, and a few holes were poked in the foil for ventilation. The precipitate was dried in oven at 80-90° C.

overnight. The precipitate was then measured out into a pre-massed, clean, labeled glass bottle, and the mass of the precipitate was recorded.

Sample preparation for antimicrobial testing was performed as follows.

A single biocide or blend of biocides was post added into white acrylic latex paint free of biocides to give a maximum total active ingredient/s concentration tested. This paint was then diluted with a biocide free acrylic latex paint to give targeted concentrations for the testing. Depending on the type of biocide blends tested, the total biocides concentrations varies from 400 to 3300 ppm. After biocides addition or dilution, each sample was hand mixed for at least a minute until uniformity was achieved. Each of the paint samples as well as a control sample (containing no biocide) were used to prepare films on black plastic-vinyl chloride/acetate copolymer panels (Leneta Company, Mahwah, N.J.) using a 0.0762 mm (3 mil) bird bar applicator. The panels were thoroughly dried for at least 2 days avoiding direct exposure to sunlight. Square discs (0.5 inch$^2$; 1.27 cm$^2$) were cut out from each panel and were used as the substrate for fungal and algal efficacy tests. This sample size allowed for an agar border when the sample disc was placed into the well of the test plate. Each sample was tested in duplicate.

The test conditions were as follows.

The appropriate media (BOLD'S 3N for Chlorophytes, BG-11 for Cyanobacteria, and PDA for fungi) were used to support microbial growth. The test plates were maintained at room temp (25° C.-26° C.), in a cycled light-dark environment, for four weeks for algae. Plates for fungal challenge tests were maintained at 30° C. for four weeks. At the end of the incubation period the samples were scored for percent area covered by visible microbial growth.

Algal inoculum was as follows.

| Organisms | abbreviation | ATCC# | Type | Medium for testing |
|---|---|---|---|---|
| Gloeocapsa sp. | Gs | ATCC 29159 | Unicellular, Colonial Cyanobacteria | BG-11 |
| Oscillatoria sp. | Os | ATCC 29135 | Filamentous Cyanobacteria | BG-11 |
| Nostoc commune | Nc | CCAP 1453/29 | Unicellular, Cenobial Chlorophyte | Bold |
| Trentepohlia aurea + Trentepohlia odorata | Ta + To | UTEX LB 429 + CCAP 483/4 | Filamentous Chlorophyte | Bold |
| Chlorella sp. UTEX + Chlorella kessleri | Cs + Ck | ATCC 30582 + ATCC 11468 | Unicellular Chlorophyte | Bold |
| Calothrix parientina | Cp | UTEX LB 1952 | Filamentous Cyanobacteria | Bold |

Fungal inoculum was as follows.

| Organisms | abbreviation | ATCC# | Medium for Growth and Testing |
|---|---|---|---|
| Aspergillus niger | An | 9642 | PDA |
| Penicillium funiculosum | Pf | 11797 | PDA |
| Cladosporium herbarum | Ch | 11281 | PDA |
| Aureobasidium pullulans | Ap | 9348 | PDA |
| Trichoderma viride | Tv | 32630 | PDA |
| Alternaria alternata | Aa | 20084 | PDA |

Algal efficacy was tested as follows (Modified ASTM 5589).

ASTM 5589 is a standard accelerated test method for determining resistance of various coatings (including paints) to algal defacement. To accommodate for high-throughput screening, this method was scaled down from petri plates to 6-well plates. A single coupon was placed with a pair of sterile forceps at the center of the agar plug (on top) with the painted surface facing upwards. Algal inoculums were prepared by mixing equal concentrations (approximately 1×10$^6$ cfu/ml) and equal volumes (depending on number of samples to be inoculated) of like growing organisms.

In this synergy study, three pool of mixed algae were prepared as the test inoculum, Gloeocapsa sp. and Oscillatoria sp. a mix of cyanobacteria grown on BG-11 media; Chlorella sp., Chlorella kessleri, and Nostoc commune are unicellular chlorphytes that were mixed and grown on Bold media; Trentepohlia aurea, Tretepohlia odorata, and Calotrix parientina are filamentous algae that were mixed and grown on Bold media.

Each well that contained a tested coupon was inoculated with 400 µl of organism mixture (approximately 1×10$^6$ cfu/ml) making sure that the whole surface (paint film as well as the agar surrounding it) was evenly covered. The plates were incubated at room temp (25° C.-26° C.) with cyclic exposure to light (OTT-Lite model # OTL4012P, 40 Watt, 26 KLumen) and dark phases, for a period of four weeks. The total area covered was evaluated at the end of each week according to percent area covered in 5% increments.

Fungal efficacy was tested as follows (Modified ASTM 5590).

ASTM 5590 is a standard accelerated test method for determining resistance of various coatings (including paints) to fungal defacement. To accommodate for high-throughput screening, this method was scaled down from petri plates to 6-well plates. To set up the test, an agar plug was placed at the bottom of each well of the sterile 6-well plate. A single coupon was placed with a pair of sterile forceps at the center of the agar plug (on top) with the painted surface facing upwards. Fungal inoculums were prepared by mixing equal concentrations (approximately 1×10$^6$ cfu/ml) and equal volumes (depending on number of samples to be tested) of like growing organisms. For this synergy study, three pools of mixed fungi were prepared as the test inoculum. Cladosporium herbarum was mixed with Trichoderma viride, Aspergillus niger was mixed with Penicillium funiculosum and Alternaria alternata was mixed with Aureobasidium pullulans. Each well was inoculated with 400 microliter of organism mixture (approximately 1×10$^6$ cfu/ml) making sure that the whole surface (paint film as well as the agar surrounding it) was evenly covered. The plates were incubated at 30° C. in presence of moisture, for a period of four weeks. The total percent area covered was evaluated and recorded at the end of each week and recorded in increments of 5%.

The Synergy Index calculation was performed as follows.

The SI is calculated based on F. C. Kull et. Al. method (Applied Microbiology, Vol. 9 (1961). In this study, SI was calculated based on the following formula with the minimum inhibitory concentration chosen based on the percent inhibitory exhibited by the individual biocide against each microorganisms tested.

$$SI = Qa/QA + Qb/QB$$

Qa=the concentration of Biocide A in the blend
QA=The concentration of Biocide A as the only biocide
Qb=The concentration of Biocide B in the blend
QB=The concentration of Biocide B as the only biocide
SI value of <1 in the formula indicates a synergism of the blended biocides exists.

Note: If any of the active with maximum concentration tested did not exhibit some inhibition, this maximum concentration is used to calculate the estimated SI and a sign of less than (<) is included to take into account that higher concentration of the active is needed to achieve the targeted inhibition NE=no end point at the concentration tested that will meet the percent inhibition criteria set in each SI calculation.

Compositions listed below that contain both zinc glyphosate and ZPT are examples of the present invention. Other compositions are comparative compositions.

Test results for Zinc Glyphosate and Glyphosic Acid are shown below:

| Active | Conc. ppm | % Inhibition Against Various Organisms Tested | | | | | |
|---|---|---|---|---|---|---|---|
| | | Cs + Ck + Nc | Cp + To + Ta | Gs + Os | Aa + Ap | An + Pf | TV + Ch |
| Zinc Glyphosate | 750 | 100 | 0 | 15 | 40 | 20 | 50 |
| | 1500 | 100 | 0 | 72.5 | 47.5 | 27.5 | 75 |
| | 2500 | 100 | 0 | 90 | 70 | 30 | 90 |
| Glyphosic Acid | 750 | 37.5 | 0 | 15 | 7.5 | 0 | 2.5 |
| | 1500 | 60 | 10 | 72.5 | 20 | 5 | 50 |
| | 2500 | 80 | 7.5 | 90 | 67.5 | 10 | 72.5 |
| Blank | | 0 | 0 | 0 | 0 | 0 | 0 |

Test Results for Zinc Glyphosate with ZPT were as follows.

| Ratios | An-Pf | Aa-Tv | Ap-Ch | Os-Gl | Ch-No | Cal-Tre |
|---|---|---|---|---|---|---|
| 1ZnGlyphosate:1ZPT | | | | | | |
| Total conc in pppm | 413 | NE | NE | 413 | 413 | 413 |
| % Inhibition | 100 | | | 100 | 80 | 100 |
| SI | <0.56 | | | 0.56 | 0.75 | 0.56 |
| 3 ZnGlyphosate:1 ZPT | | | | | | |
| Total conc in pppm | 412 | NE | NE | 1650 | 412 | 412 |
| % Inhibition | 100 | | | 100 | 100 | 60 |
| SI | <0.78 | | | 3.125 | 0.62 | 0.78 |
| 5ZnGlyphosate:1 ZPT | | | | | | |
| Total conc in pppm | 825 | NE | NE | 2475 | 825 | 825 |
| % Inhibition | 100 | | | 100 | 80 | 100 |
| SI | <1.71 | | | 5.125 | 1.17 | 1.71 |
| 10ZnGlyphosate:1 ZPT | | | | | | |
| Total conc in pppm | 825 | NE | NE | 1650 | 3300 | 825 |
| % Inhibition | 100 | | | 100 | 60 | 80 |
| SI | <1.84 | | | 3.68 | 4.36 | 1.84 |
| 1ZnGlyphosate:10 ZPT | | | | | | |
| Total conc in pppm | 825 | NE | NE | 1650 | 3300 | 2475 |
| % Inhibition | 80 | | | 100 | 60 | 100 |
| SI | <0.41 | | | 0.82 | 7.64 | 1.23 |
| 1ZnGlyphosate:5 ZPT | | | | | | |
| Total conc in pppm | 825 | NE | NE | 3300 | 1650 | 825 |
| % Inhibition | 80 | | | 80 | 80 | 100 |
| SI | <0.54 | | | 2.17 | 3.67 | 0.54 |
| 1ZnGlyphosate:3 ZPT | | | | | | |
| Total conc in pppm | 412 | NE | NE | 3300 | 3300 | 825 |
| % Inhibition | 0.8 | | | 80 | 80 | 60 |
| SI | <0.34 | | | 2.75 | 7.00 | 0.69 |
| ZnGlyphosate | | | | | | |
| Total conc in pppm | 412.5 | NE | NE | 412.5 | 825 | 412.5 |
| % Inhibition | 100 | | | 100 | 80 | 100 |
| ZPT | | | | | | |
| Total conc in pppm | 3300 | NE | NE | 3300 | 412.5 | 3300 |
| % Inhibition | 0 | | | 100 | 80 | 40 |

Combinations with ratio of ZPT:Zinc Glyphosate of 0.33:1 to 10:1 show especially effective synergy.

The invention claimed is:

1. A synergistic antimicrobial composition comprising a) zinc pyrithione and b) zinc glyphosate present in an effective amount to control fungi and algae wherein the weight ratio of zinc pyrithione to zinc glyphosate is 3:1 to 10:1.

2. A method of inhibiting the growth of or controlling the growth of fungi or algae in a building material, said method comprising the step of adding the synergistic antimicrobial composition of claim 1 to said building material.

3. A coating composition comprising the synergistic antimicrobial composition of claim 1.

4. A dry film made by a process comprising applying a layer of the coating composition of claim 3 to a substrate and drying said coating composition or allowing said coating composition to dry.

* * * * *